US00PP25996P3

(12) United States Plant Patent
Lugli et al.

(10) Patent No.: US PP25,996 P3
(45) Date of Patent: Oct. 20, 2015

(54) CHERRY TREE NAMED 'PA1UNIBO'

(50) Latin Name: *Prunus avium*
Varietal Denomination: PA1UNIBO

(71) Applicant: Alma Mater Studiorum-Università degli Studi di Bologna, Bologna (IT)

(72) Inventors: Stefano Lugli, Modena (IT); Riccardo Correale, Bologna (ID); Michelangelo Grandi, Castenaso (IT)

(73) Assignee: Alma Mater Studiorum-Università degli Studi di Bologna, Bologna (IT)

( * ) Notice: Subject to any disclaimer, the term of this patent is extended or adjusted under 35 U.S.C. 154(b) by 118 days.

(21) Appl. No.: 13/986,702

(22) Filed: May 28, 2013

(65) Prior Publication Data

US 2013/0326772 P1 Dec. 5, 2013

(30) Foreign Application Priority Data

May 25, 2012 (QZ) ..... PBR 2012/1157

(51) Int. Cl.
*A01H 5/00* (2006.01)
*A01H 5/08* (2006.01)

(52) U.S. Cl.
USPC ..... Plt./181
CPC ..... *A01H 5/085* (2013.01)

(58) Field of Classification Search
USPC ..... Plt./181
See application file for complete search history.

*Primary Examiner* — Annette Para
(74) *Attorney, Agent, or Firm* — Hershkovitz & Associates, PLC

(57) ABSTRACT

Variety Denomination 'PA1UNIBO' is a novel cherry tree derived from a seedling of unknown cross which was planted at Vignola, Modena Province, Italy. The genus and species (cultivar) of 'PA1UNIBO' is *Prunus avium*. It was initially propagated by grafting to root stocks of varying vigor and, after testing in districts and plantings of differing types, proved to have the qualities proper to a promising new cultivar for the market.

5 Drawing Sheets

Latin name of the genus/species of the plant claimed (cultivar): *Prunus avium.*

Variety denomination: PA1UNIBO.

CROSS-REFERENCE TO RELATED APPLICATIONS

This application claims priority of the pending EU Plant Patent for 'PA1UNIBO', which was filed on 25 May 2012 as Application No. 2012/1157 in the name of Applicant (holder) Alma Mater Studiorum—Università degli Studi di Bologna, the contents of which are expressly incorporated herein by reference. EU Trademark for 'Sweet Aryana' was released on 2 Jan. 2013 as Registration No. 011058559 of Applicant (holder) Alma Mater Studiorum—Università degli Studi di Bologna. Such European Trademark is associated to PA1UNIBO and used to distinguish such cherry variety from the others.

BACKGROUND OF THE INVENTION

*Prunus avium* 'PA1UNIBO' originally derived from seedling of unknown cross and called Selection DCA BO A1A1, was planted at Vignola, Modena Province, Italy, in February 2002, and was first cropped in 2004. It was initially propagated by grafting to root stocks of varying vigor, tested in different growing districts and planting densities, and proved to have the properties proper to a promising new cultivar for the market. It picks in the last decade of May to the first decade in June in Modena Province, more precisely, about 3-5 days after 'Burlat' and approximately 13-15 days before 'Bing'.

BRIEF SUMMARY OF THE INVENTION

The parentage of the variety is unknown. The name of a known variety with approximate comparable harvest date is 'Burlat' (e.g., 'Bing' ripens approximately 18 days after 'Burlat'). However, compared to 'Burlat', its fruit is larger, comparable in size to 'Duroni 3' and 'Sunburst' varieties, of firmer flesh, with more uniform ripening and higher sugar content. 'PA1UNIBO', also known as 'Sweet Aryana', was selected for its high qualities, including tree growth and yield performance, fruit appearance and excellent taste-flavor properties, very sweet and with a good level of acidity. The distinctive traits of 'PA1UNIBO' also include early an picking date, uniform ripening with excellent stability of maturation that guarantees collection of over 10 days, large-sized fruit, and excellent flesh firmness. Both the skin and flesh are dark red brilliant (scale 5 CTIFL). The date of cross was in the year 2000. The location of the discovery was Vignola, Modena Province, Italy. The date of the first asexual propagation was in 2008 in Vignola, Modena Province, Italy. PA1UNIBO was first propagated by grafting on 'Colt' (U.S. Plant Pat. No. 4,059) and 'Gisela 6' (U.S. Plant Pat. No. 8,954) root stocks of differing vigor in trial fields of Bologna University, to test growth and yield performance under differing training systems and planting densities.

BRIEF DESCRIPTION OF THE DRAWINGS

The accompanying photographs show typical specimens of the new variety as depicted in color as nearly true as is reasonably possible in color illustrations of this character.

DETAILED BOTANICAL DESCRIPTION OF THE PLANT CLAIMED

Figure 1:
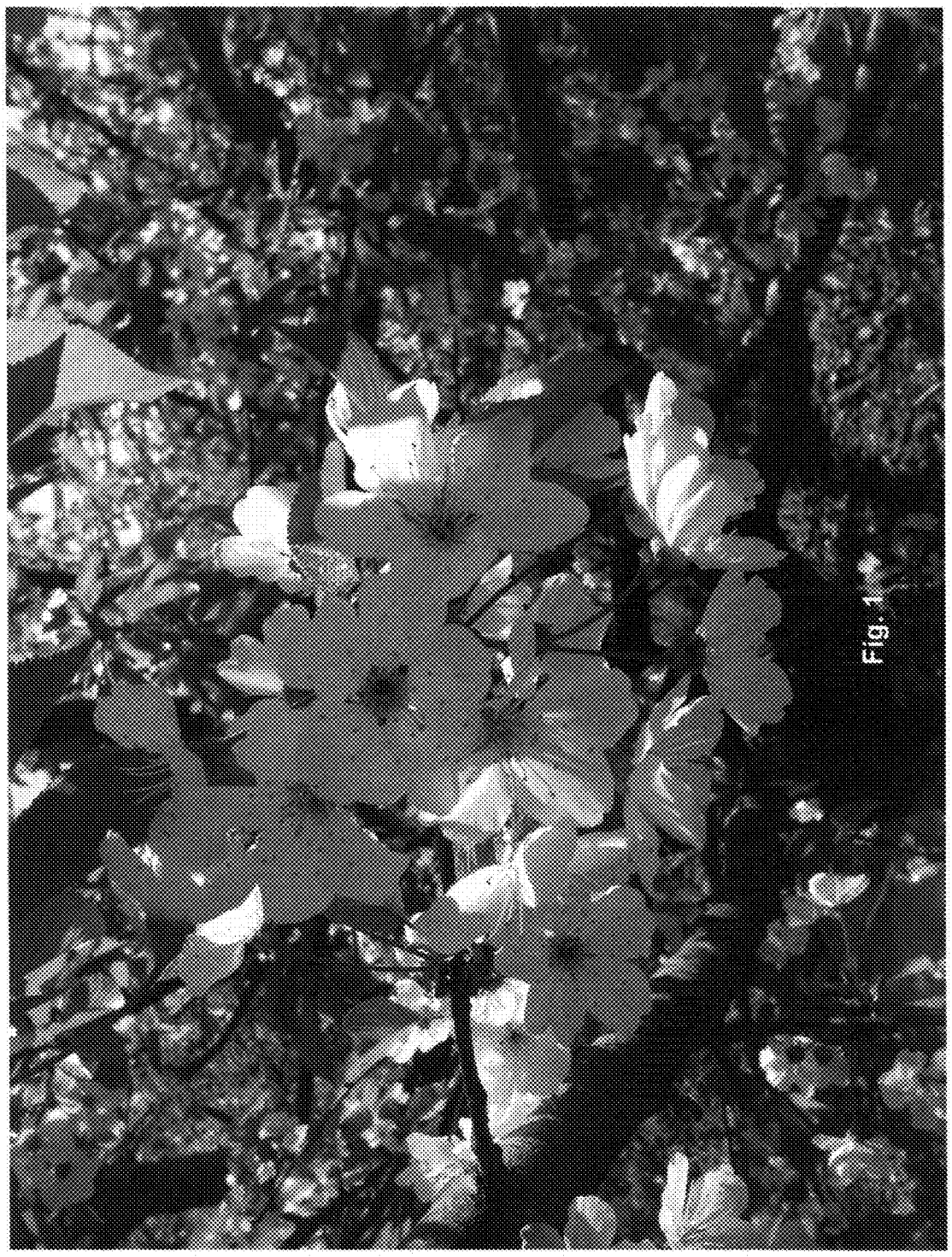
FIG. 1 illustrates the open, semi-spreading tree architecture with fully-open blossoms of PA1UNIBO.
Figure 2:
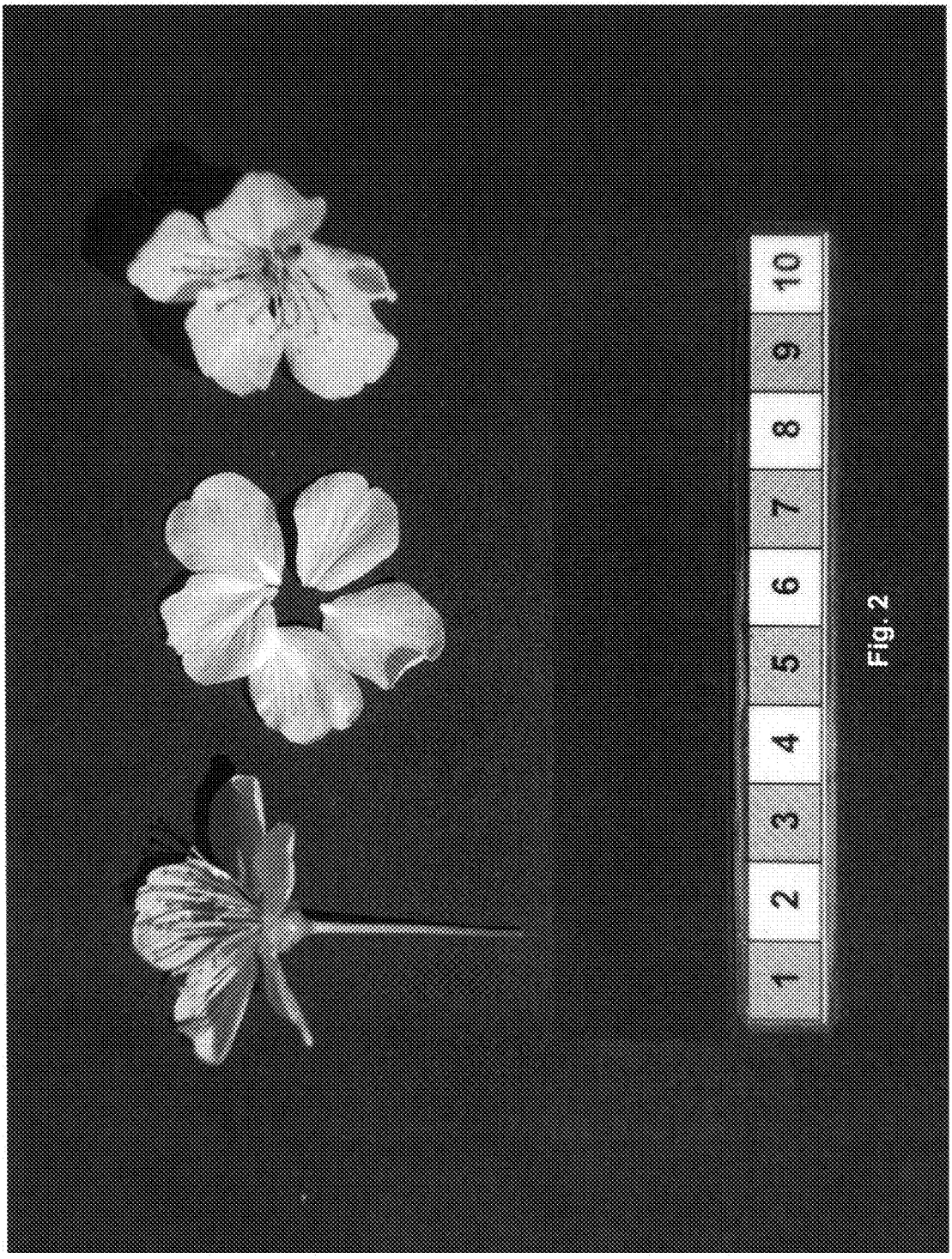
FIG. 2 is the flower, full front, in profile and with separated petals, of PA1UNIBO.
Figure 3:
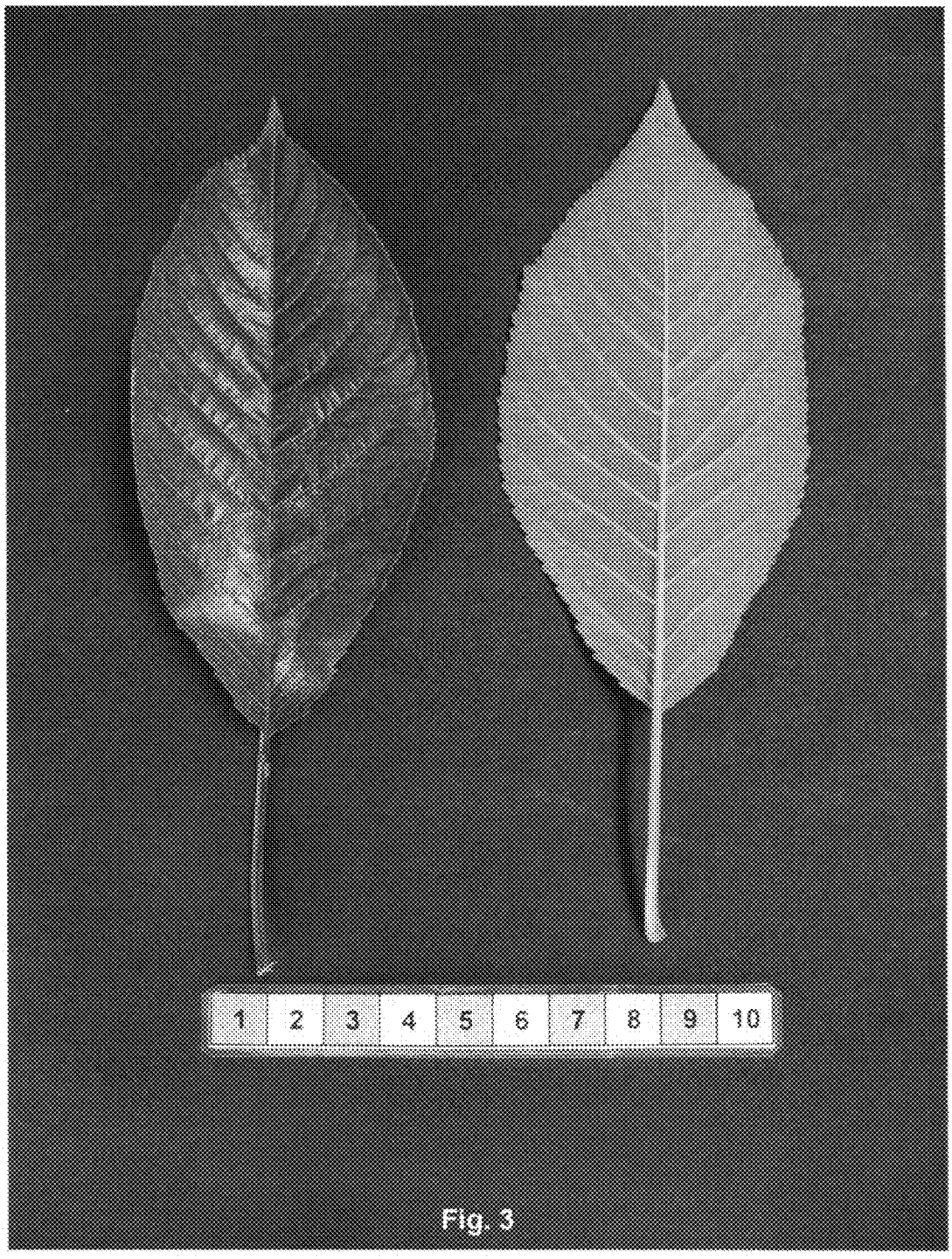
FIG. 3 shows the leaf profile of PA1UNIBO. Two leaves have been detached and one has been placed upper leaf surface side down to show the lower leaf surface details.
Figure 4:
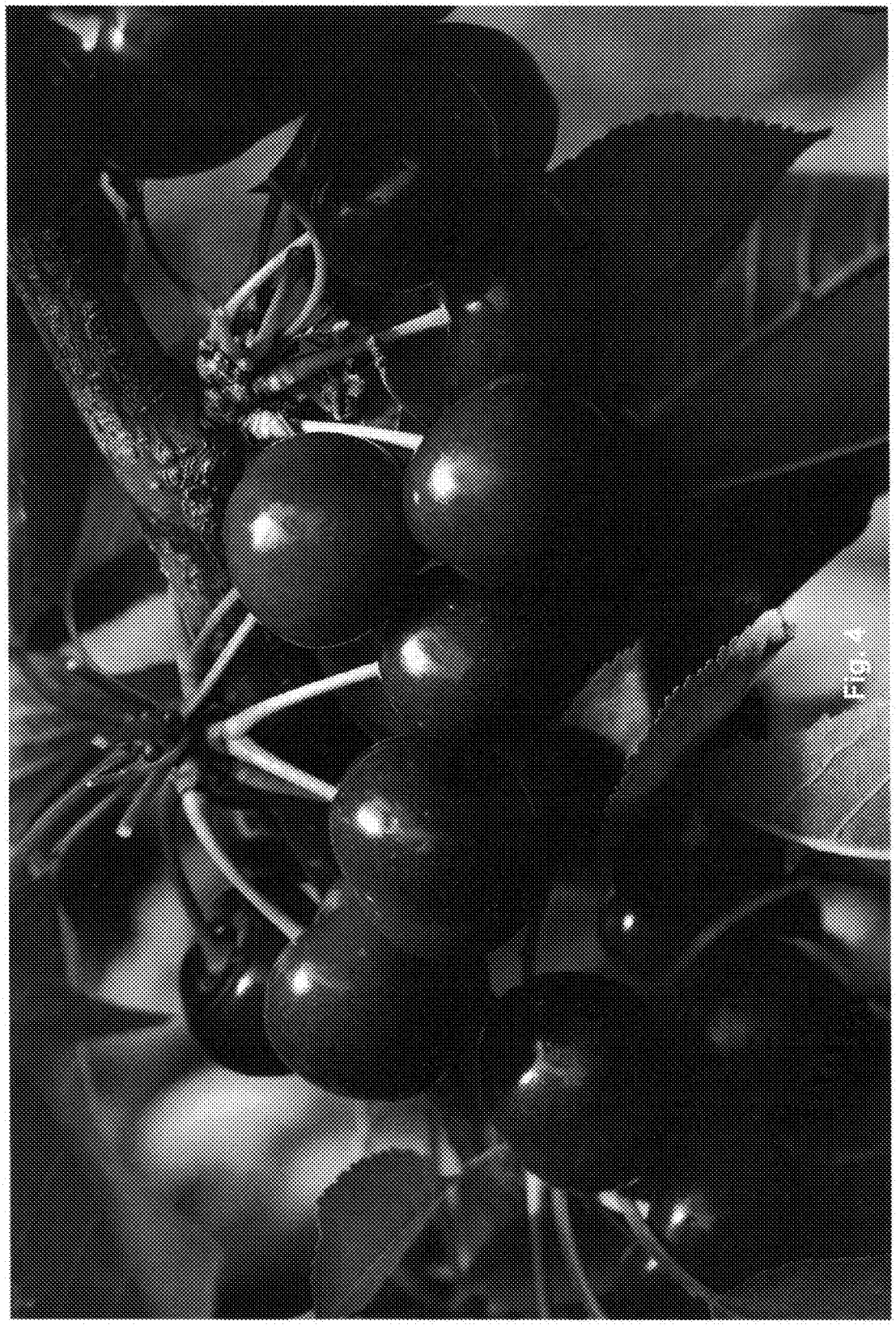
FIG. 4 is a close-up of the fruit cropping of PA1UNIBO.
Figure 5:
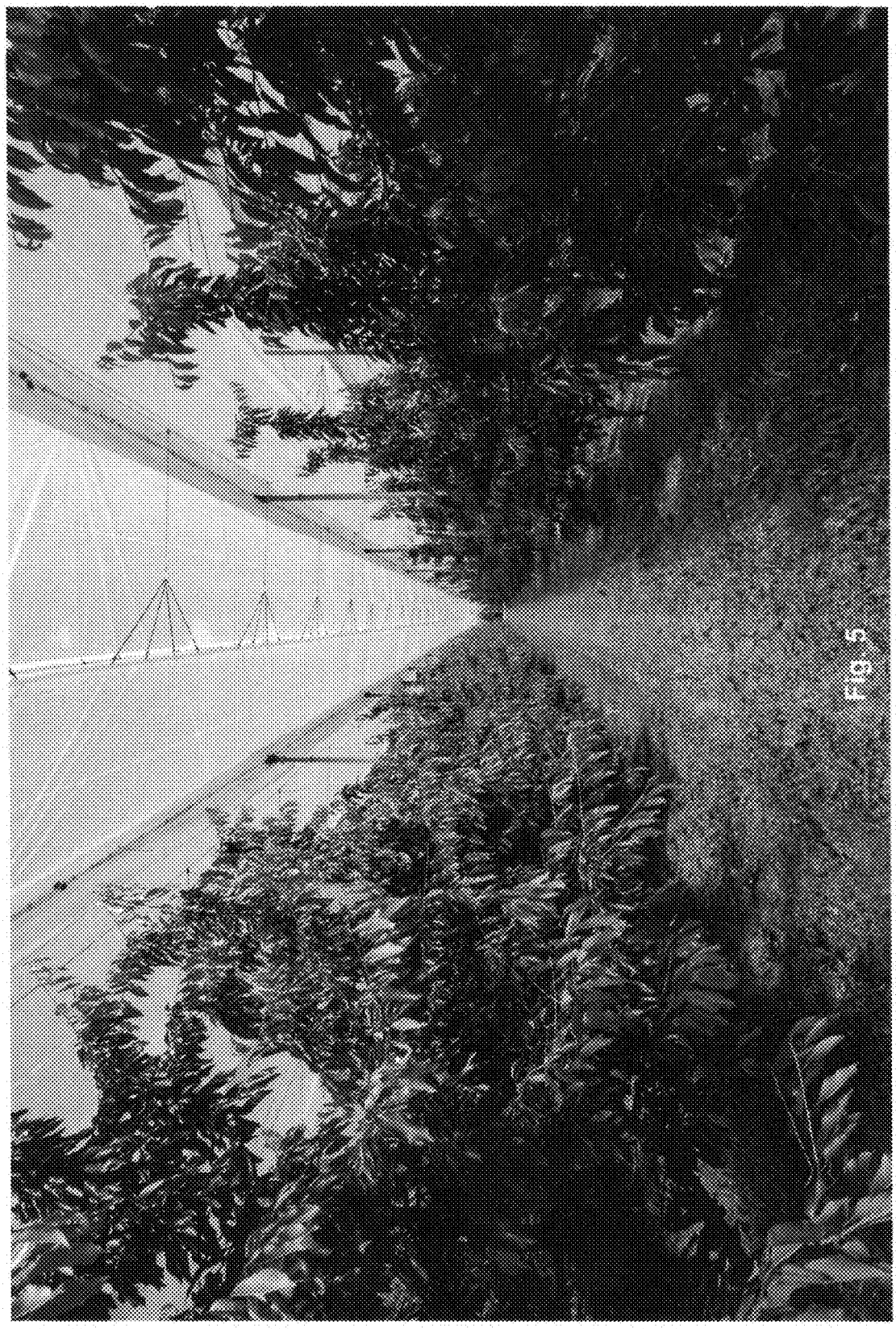
FIG. 5 shows the tree habit, with width-spread and height, of PA1UNIBO.

General:
- *Age of described tree(s).*—5 years, multi-leader spindle.
- *Location of described trees(s).*—Vignola, Modena Province, Italy.
- *Name of color chart used.*—Royal Horticultural Society Colour Chart.
- *Name of root stock.*—'Colt'.

Tree:
- *Vigor.*—High.
- *Height.*—4.5 meters.
- *Spread.*—3 meters.
- *Growth habit.*—Open.
- *Canopy density.*—Medium.
- *Trunk diameter at specified height.*—16-20 cm, as measured at about 5 cm above graft joint.
- *Trunk color.*—Reddish-brown (200C) flecked with gray (201A).
- *Bark texture.*—Medium rough.
- *Tendency toward alternate bearing.*—No.
- *Winter hardiness.*—Unknown; no winter cold damage found in this Po Valley district.
- *Chilling requirement.*—Unknown.

Branch:
- *Length.*—300-400 cm.
- *Diameter.*—5-6 cm.
- *Crotch angle.*—45°-60° depending on training system.
- *Bark color.*—Brown (200B) flecked with red (183A).
- *Bark texture.*—Medium rough.

Current year shoot:
- *Length.*—40-65 cm.
- *Color.*—Reddish-brown (200C/200D) with fairly widespread gray overtone (201A).

Winter hardiness:
- *USDA hardiness zone.*—Unknown.
- *Chilling requirement.*—Unknown.

Flower buds:
- *Number per spur.*—4-6, but usually 5.
- *Shape.*—Sub-globose.
- *Length.*—About 1 cm.
- *Diameter.*—Under 1 cm.
- *Color.*—Reddish perules (187C).

Flowers:
- *Number per cluster.*—Minimum 7, maximum 9 per spur; 2-3 per bud. Bloom is abundant.
- *Relative position of petals.*—Petals overlap slightly.
- *Diameter.*—32-37 mm.
- *Depth.*—13-15 mm, measured as distance from receptacle to maximum petal aperture.
- *Is pollen produced?.*—Yes.
- *Coloration of pollen.*—Pale yellow (12A).

Sepal:
- *Length.*—5-7 mm.
- *Shape.*—Heart-shaped.
- *Width.*—About 5 mm.
- *Apex.*—Pointed.
- *Base.*—Flat.
- *Margin descriptors.*—Regular margin.
- *Color—upper surface.*—Pale green (138C).
- *Color—lower surface.*—Pale green (138C).

Petal:
- *Number per flower.*—5.
- *Shape.*—Circular.
- *Length.*—14-16 mm.
- *Width.*—15-17 mm.
- *Apex.*—Slightly sunken.
- *Base.*—Slightly pointed.
- *Margin.*—Slightly undulated.
- *Color—upper surface.*—White (155B).
- *Color—lower surface.*—White (155B).

Bloom:
- *Date of bud burst.*—7-8 Apr. 2013.
- *Date of first bloom.*—13 Apr. 2013.
- *Date of full bloom.*—16 Apr. 2013.

Pedicel:
- *Length.*—33-36 mm.
- *Diameter.*—About 1.2 mm.
- *Color.*—Pale green (143C).

Pistil:
- *Quantity.*—1.
- *Size.*—19-23 mm.
- *Color.*—Pale green (143D).

Anthers:
- *Quantity.*—22-25, with about 70% of 10-13 mm in length, positioned slightly below the top of the stigma, and the remaining 30% varying from 5-8 mm. White filament (155D).
- *Size.*—About 1 mm diameter.
- *Color.*—Orange-yellow (15A).

Stigma:
- *Quantity.*—1.
- *Size.*—1.1-1.3 mm diameter.
- *Color.*—Pale green (142B).

Styles:
- *Quantity.*—1.
- *Size.*—14-16 mm length.
- *Color.*—Pale green (142B) at basal and distal parts, white-green (142D) in center turning to rosé (36C) at end of bloom.

Ovary/ies:
- *Quantity.*—1.
- *Size.*—5-7 mm.
- *Color.*—Pale green (143D).

Leaves:
- *Length.*—11.8-12.4 cm.
- *Width.*—6.1-6.8 cm.
- *Shape.*—Lanceolate-elliptical.
- *Apex shape.*—Pointed.
- *Base shape.*—Pointed.
- *Margin.*—Fine toothed.
- *Color—upper surface.*—Dark green (137A).
- *Color—lower surface.*—Pale green (138A/138B) veined green-yellow (152A/152B) in center.

Petiole:
- *Length.*—4.1-4.5 cm.
- *Diameter.*—About 2 mm.
- *Color.*—Green-yellow lower (152A/152B) and reddish upper (183A).

Fruit:

*Shape.*—Depressed heart-shaped.

*Diameter.*—Mostly 28 mm.

*Height.*—21-24 mm.

*Weight.*—11-12 grams on average.

*Number per cluster.*—5-10 per spur.

*Skin color* (*include ground color and over color*).—Shiny dark red (187B) tending to blackish-dark red (187A) at advanced maturity.

*Presence of lenticels.*—Yes.

*Density of lenticels.*—Medium.

*Skin thickness.*—Medium-thin.

*Skin texture.*—Medium.

*Anthocyanin coloration present near skin*?.—No.

*Tenacity of flesh to stone.*—Low.

*Flesh color.*—Red (53A).

*Flesh texture.*—Fine.

*Juiciness.*—High.

*Juice analysis* (*brix, acidity, tss, etc.*).—17.6° Brix and 8.6 g/l malic acid (2012 data).

*Stone size.*—Medium-small.

*Stone shape.*—Elliptical.

*Stone color.*—Pale brown (165D).

Fruit stem:

*Length.*—35-38 mm.

*Diameter.*—Just over 1 mm.

*Color.*—Green (143A).

Harvest:

*Maturity date range.*—May 20-June 10, approximately 5 days after 'Burlat' and about 13 to 15 days before 'Bing'. Optimum harvest dates of 'PA1UNIBO' in Modena Province are May 25-June 1.

*Harvest date range* (*if different*).—Same as above.

The diploid cultivar 'PA1UNIBO' is self-fertile, with the allelic profile of S3S4'. Fruit load and yield is high and constant, particularly in the presence of flying insects (e.g., bees, wasps, hornets, beetles, butterflies, etc.).

Under observation during planting, growing and harvesting under normal cultural and growing conditions in Modena Province, Italy, no particular insect or plant/fruit disease resistance or susceptibility has been observed.

Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed is:

1. A new and distinct cherry tree as herein described and illustrated.

* * * * *